United States Patent

Eaton

[11] Patent Number: 6,074,420
[45] Date of Patent: Jun. 13, 2000

[54] FLEXIBLE EXINT RETENTION FIXATION FOR EXTERNAL BREAST PROSTHESIS

[75] Inventor: L. Daniel Eaton, Little Rock, Ark.

[73] Assignee: Board of Trustees of the University of Arkansas, Little Rock, Ark.

[21] Appl. No.: 09/227,789

[22] Filed: Jan. 8, 1999

[51] Int. Cl.⁷ .................................. A61F 2/52; A61F 2/12
[52] U.S. Cl. ...................................................... 623/7; 623/8
[58] Field of Search .............................. 623/7, 66, 9, 10, 623/11

[56] References Cited

U.S. PATENT DOCUMENTS

| | | |
|---|---|---|
| 3,897,376 | 7/1975 | Lampe . |
| 3,925,277 | 12/1975 | Lampe . |
| 4,004,298 | 1/1977 | Freed . |
| 4,154,226 | 5/1979 | Hennig et al. . |
| 4,258,705 | 3/1981 | Sorensen et al. . |
| 4,549,529 | 10/1985 | White . |
| 4,824,371 | 4/1989 | Deutsch et al. . |
| 4,997,372 | 3/1991 | Shiner et al. . |
| 5,071,433 | 12/1991 | Naestoft et al. . |
| 5,230,694 | 7/1993 | Rosenblum . |
| 5,314,478 | 5/1994 | Oka et al. . |
| 5,344,457 | 9/1994 | Pilliar . |
| 5,352,307 | 10/1994 | Wild . |
| 5,376,323 | 12/1994 | Eaton . |
| 5,425,763 | 6/1995 | Stemmann . |
| 5,527,359 | 6/1996 | Nakamura et al. . |
| 5,569,223 | 10/1996 | Titone et al. . |
| 5,607,473 | 3/1997 | Weber-Unger et al. . |
| 5,700,288 | 12/1997 | Eaton . |
| 5,855,606 | 1/1999 | Eaton . |

FOREIGN PATENT DOCUMENTS

| | | |
|---|---|---|
| 392960 | 10/1990 | European Pat. Off. . |
| 4115428 | 11/1992 | Germany . |
| 2202745 | 10/1988 | United Kingdom . |

OTHER PUBLICATIONS

Holt, "Osscointegrated Implants in Oro–dental and Facial Prosthetic Rehabilitation," Craniofacial Skelton Augmentation and Replacement, vol. 27, No. 5, Oct. 1994, Otolaryngologic Clinics of North America, pp. 1001–1014.

Primary Examiner—David J. Isabella
Attorney, Agent, or Firm—Ray F. Cox, Jr.

[57] ABSTRACT

An external prosthesis and a method for affixing the prosthesis to the user by means compliantly housed magnets interacting with surgical steel implants inserted beneath the skin of the user. The implants are surgical steel buttons coated with methylmethacrylate to avoid the release of corrosion products and silastic, a biocompatible material. The implant is inserted beneath the patient's skin along with a biocompatible mesh material to provide additional strength. A flexible carrier is formed with a hollow cylindrical shape to allow a magnet to move freely within the carrier. The opening of the flexible carrier is covered with a mesh. The flexible carrier/magnet/mesh combination is formed into the prosthesis so that the prosthesis aligns with the surgical steel implants and allows freedom of movement within the flexible carrier. The mesh material allows for breathability and also avoids skin strangulation from excess pressure of the magnet on the surgical steel implant.

30 Claims, 3 Drawing Sheets

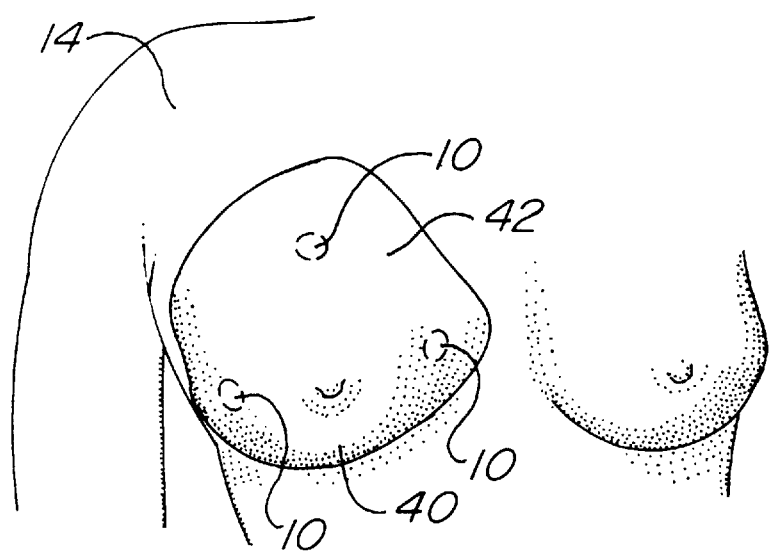
FIG. 8
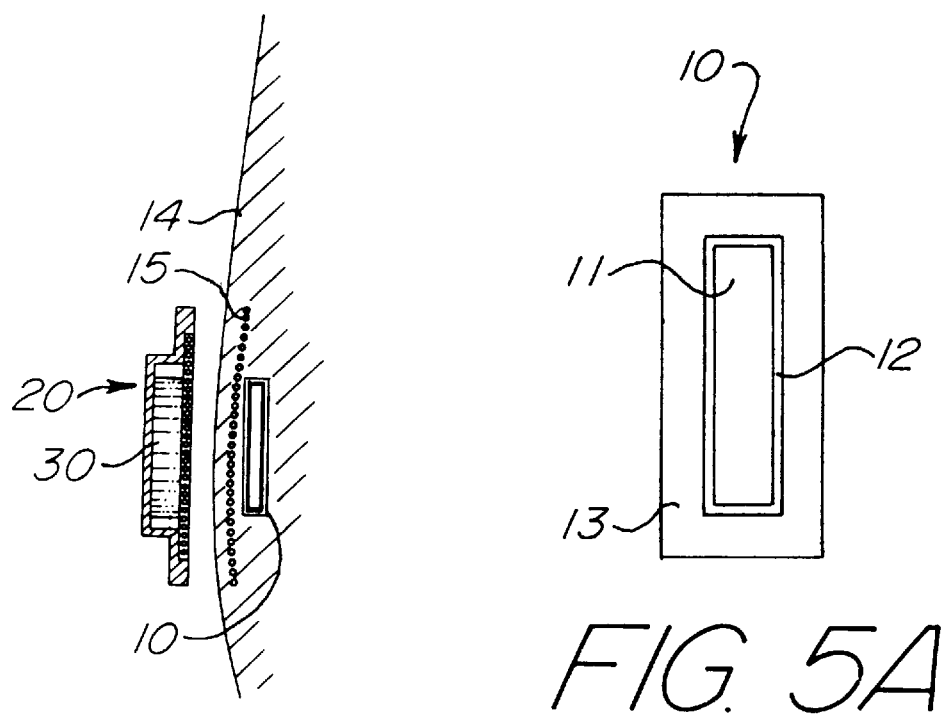
FIG. 5
FIG. 5A

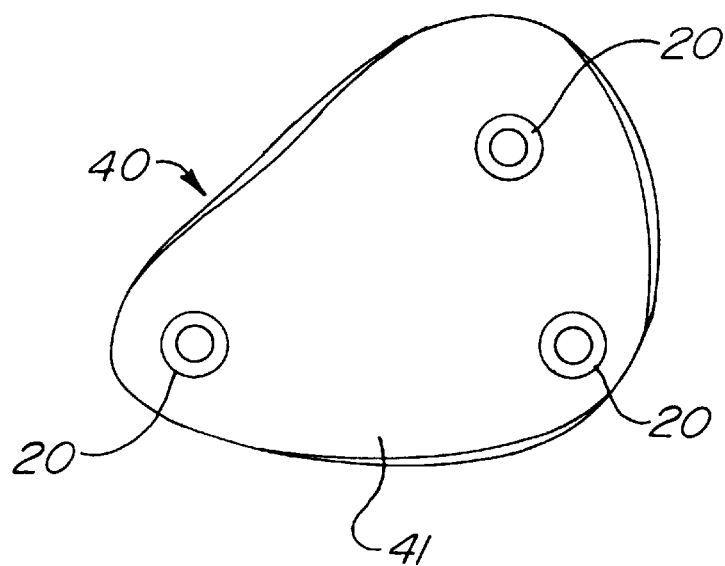
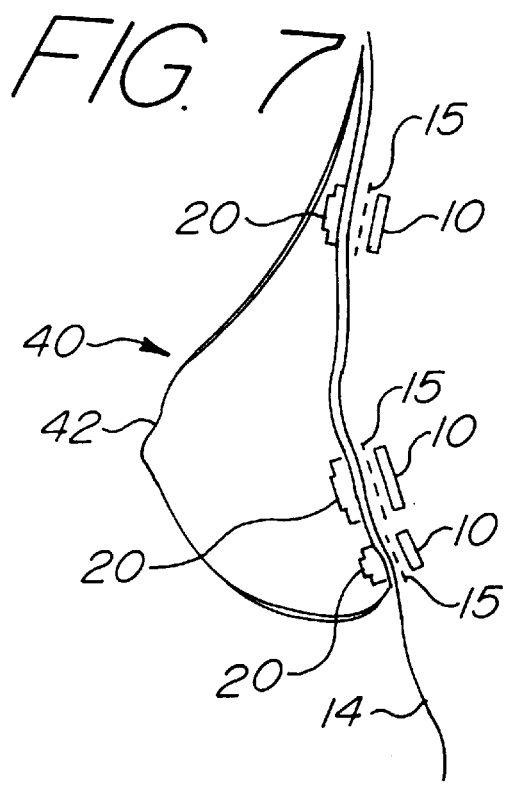

FLEXIBLE EXINT RETENTION FIXATION FOR EXTERNAL BREAST PROSTHESIS

BACKGROUND OF THE INVENTION

The present invention relates to an external prosthesis and a device and method for affixing the prosthesis to the user by means of magnets compliantly housed in the prosthesis for interaction with surgical steel implants surgically inserted beneath the skin of the user. The present invention relates in particular to breast prostheses.

Various techniques are known for affixing prostheses to a user by means of magnets. For example, Stemmann (U.S. Pat. No. 5,425,763) discloses a magnet arrangement for fastening prostheses employing two or more magnets that are displaceable telescopically relative to each other to provide flexibility in the fixation of the prosthesis. One magnet is affixed to the body of the user and the other magnet is part of the prosthesis. Stemmann discloses the body-attached portion to be osseointegrated. The body-attached magnet and the prosthesis magnet are housed in titanium containers, although it is also disclosed that the containers can be of any body compatible material. Stemmann does not disclose an implant of a ferromagnetic material such as stainless steel, nor does Stemmann disclose the use of a single magnet housed within a flexible carrier.

Shiner et al. (U.S. Pat. No. 4,997,372) is typical of a number of patents disclosing magnetic fixation devices for dental prostheses. Deutsch et al. (U.S. Pat. No. 4,824,371) is also a dental fixation device employing magnets.

Freed (U.S. Pat. No. 4,004,298) discloses a connector using complementary magnetic fields to align the connector.

Sorensen et al. (U.S. Pat. No. 4,258,705) and Hennig et al. (U.S. Pat. No. 4,154,226) disclose systems employing two or more magnets to seal body openings.

Nielsen (EPO Patent Application 0392960) discloses a breast prosthesis aggregate comprising a flexible breast prosthesis and one or more fastening slabs sealable to the skin of the wearer by means of adhesive. While the primary sealing means disclosed in the application is hook and loop fastening material, it is also disclosed that the attachment slabs adhered to the skin of the wearer may be magnetic and the prosthesis may incorporate permanent magnets. Plass (UK Patent Application 2202745A) similarly discloses an adhesive attachment means employing hook and loop fastening material.

Titone et al. (U.S. Pat. No. 5,569,273) disclose a polypropylene surgical mesh.

It is desirable to provide for a prosthesis fixation method which combines the surgical implantation of a surgical stainless steel button along with a flexible carrier housing a permanent magnet with space available for a degree of freedom of movement of the magnet with respect to the flexible carrier. It is also desirable for implants to be biocompatible through the combination of layers of methymethacrylate and silastic. Furthermore, the use of a biocompatible mesh material to improve the strength of the implantation is desirable.

The limitations of the prior art are overcome by the present invention as described below.

SUMMARY OF THE INVENTION

The present invention is a breast prosthesis and a device and method for affixing the breast prosthesis to the user by means of surgical steel implants surgically inserted beneath the skin of the user. Although the invention is primarily directed to a breast prosthesis, the invention is not so limited and may also be used for affixing other external prostheses such as prostheses of the head and neck region, ear, etc.

The implants used in this invention are surgical steel buttons coated with methylmethacrylate and silastic. The methylmethacrylate coating is intended to prevent any corrosion products from the surgical steel being released into the tissues of the patient. The silastic is coated over the methylmethacrylate layer. It is a biocompatible material and provides an additional degree of security against corrosion products from the surgical steel. The methylmethacrylate coating is approximately 0.1 millimeter thick and the silastic overcoat is approximately 1.0 millimeter thick.

The surgical steel implant is surgically inserted two to three millimeters beneath the patient's skin. A biocompatible mesh material of somewhat greater diameter than that of the implant is inserted into the incision above the surgical steel implant. The mesh may be of Teflon or similar material. The purpose of the mesh is to provide additional strength to the portion of the patient's skin over the implant.

A flexible carrier, desirably made of silastic, is formed with a hollow cylindrical shape to hold a magnet, such as a neodymium type. The hollow cylindrical interior of the flexible carrier is sized to allow the magnet to move freely back and forth. The opening of the flexible carrier is covered with a mesh which is desirably made of Teflon. The mesh may also be made of other biocompatible material such as polypropylene. The flexible carrier/magnet/mesh combination is formed into the prosthesis so that the prosthesis, when placed next to the skin of the patient, aligns with the previously implanted surgical steel implants. Since the magnets are allowed a certain degree of freedom of movement within the flexible carrier, the prosthesis is allowed to flex and move with respect to the patient's skin without unnecessary binding.

The mesh material over the opening of the flexible carrier prevents the magnet from coming into direct contact with the patient's skin. This allows for breathability and also avoids skin strangulation from excess pressure of the magnet on the surgical steel implant.

It is therefore an object of the present invention to provide for an external prosthesis which may be securely affixed to a user without the use of adhesive to affix the prosthesis or parts of the prosthesis to the user.

It is a further object of the present invention to provide for an external prosthesis which is affixed by compliant means allowing a more nearly natural flexibility of movement of the prosthesis with respect to the user.

These and other objects and advantages of the present invention will be apparent from a consideration of the following detailed description of the preferred embodiments in conjunction with the appended drawings as described following.

BRIEF DESCRIPTION OF THE DRAWINGS

FIG. 5 is a sectional side elevational view of the flexible carrier with permanent magnet juxtaposed to the surgical steel implant.

FIG. 5A is an enlarged sectional side elevational view of the surgical steel implant.

FIG. 6 is posterior elevational view of a breast prosthesis with a plurality of flexible carriers.

FIG. 7 is a sectional side elevational view of the breast prosthesis of FIG. 6 juxtaposed to a matching array of surgical steel implants beneath the skin of a user.

FIG. 8 is an anterior elevational view of the breast prosthesis of FIG. 7 affixed to a user showing the surgical steel implants in shadow outline.

DETAILED DESCRIPTION OF THE PREFERRED EMBODIMENTS

Figure 1:
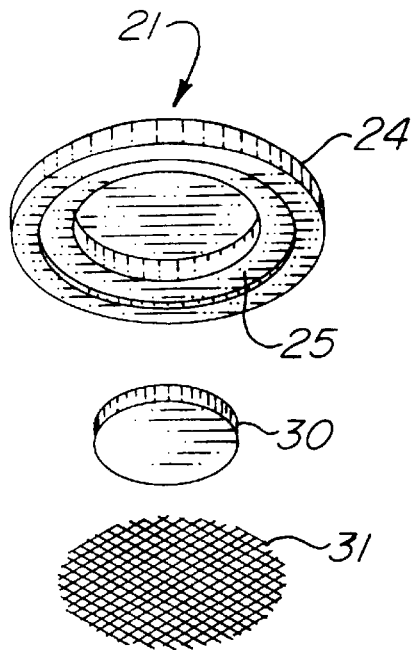
FIG. 1 is an exploded isometric view of the flexible carrier.
Figure 2:
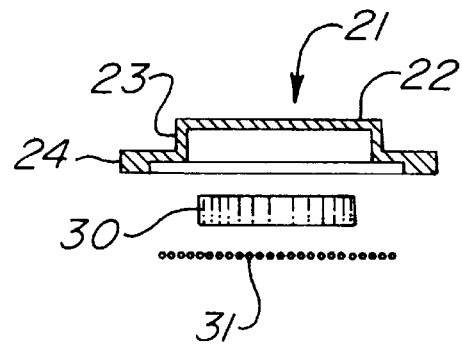
FIG. 2 is an exploded sectional side elevational view of the flexible carrier of FIG. 1.

With reference to FIGS. 1–8, the preferred embodiment of the present invention may be described. A significant objective in affixing an external prosthesis to a user is that the prosthesis should not only replicate the appearance of the natural anatomy but should offer a natural and comfortable feel to the user. Ideally, the prosthesis should be no more noticeable to the user than the original anatomy replicated by the prosthesis. Prostheses however tend to be less flexible and mobile than natural anatomy. The present invention addresses this problem by providing for a means of affixing the prosthesis to the body of the wearer using a compliant magnetic means to allow for greater flexibility and freedom of movement of the prosthesis with respect to the user.

The present invention therefore provides for an external prosthesis and a method for affixing the external prosthesis to the user by means of compliantly housed magnets in the prosthesis which interact with surgical steel implants surgically inserted beneath the skin of the user. Although the invention is primarily directed to a breast prosthesis, the invention is not so limited and may also be used for affixing other external prostheses such as prostheses of the head and neck region, ear, etc.

With reference to FIG. 5A, the implant 10 used in this invention is a button 11 of surgical steel coated with a inner methylmethacrylate layer 12 and an outer silastic layer 13. The inner methylmethacrylate layer 12 is a coating intended to prevent any corrosion products from the surgical steel button 11 being released into the tissues of the patient. Materials other than methylmethacrylate may be employed as a corrosion barrier. The outer silastic layer 13 is coated over the methylmethacrylate layer 12. Silastic is a biocompatible material and additionally provides an additional degree of security against corrosion products from the surgical steel button 11. Materials other than silastic may be employed to provide the biocompatible layer. The methylmethacrylate layer 12 is desirably approximately 0.1 millimeter thick and the silastic layer 13 is desirably approximately 1.0 millimeter thick. The surgical steel button 11 is desirably of stainless steel which is both resistant to corrosion and is ferromagnetic to allow for magnetic interaction with a permanent magnet. Other types of ferromagnetic materials are contemplated as being within the scope of the present invention.

As shown with reference to FIG. 5, the surgical steel implant 10 is surgically inserted two to three millimeters beneath the user's skin 14. A biocompatible mesh 15 of somewhat greater diameter than that of the implant 10 is inserted into the incision above the surgical steel implant 10. The mesh 15 may be of Teflon or similar material. The purpose of the mesh 15 is to provide additional strength to the portion of the user's skin 14 over the implant 10. As will be described hereinafter, the implant 10 interacts magnetically with a permanent magnet to affix the prosthesis to the user. Sufficient magnetic force to hold the prosthesis firmly to the user is desirable to avoid accidentally dislodging the prosthesis, but the amount of force required to remove the prosthesis may then produce significant pulling forces on the implant 10. To avoid tearing or distorting the incision, the area of skin 14 above the implant 10 is desirably reinforced by the addition of the mesh 15. The prosthesis may then be safely and comfortably affixed and removed as often as needed.

The following is a description of the surgical procedure for implanting the implants 10 in the case of a breast prosthesis. The procedure for other types of prostheses is essentially the same.

The surgical procedure for implanting an implant 10 begins with selecting the sites for positioning each implant 10. Facing the patient, sites are chosen 20 millimeters inside the outer perimeter edge of the prosthesis. For a breast prosthesis, three sites could be chosen at approximately 10 o'clock medially, 12 o'clock superiorly, and 3 o'clock laterally for a left prosthesis and 2 o'clock medially, 12 o'clock superiorly and 9 o'clock laterally for a right prosthesis. Intercostal space position is desirable. For other types of prostheses, fewer implants might be desirable. In some cases only a single implant would be acceptable.

The site is anesthetized and the first incision peripheral to the implant site is made. An oblique incision is recommended going to a depth of approximately 2–3 millimeters and a pocket is dissected large enough to accommodate both the implant 10, typically about 14 millimeters by 3 millimeters, and the overlying biocompatible mesh 15. A suitable mesh material is a polypropylene surgical mesh of the type offered by Atrium Medical Corporation, 5 Wentworth Dr., Hudson, N.H. 03051.

A trial implant is inserted into the wound to evaluate fit. No puckering of the skin should be observed and the incision margins should close spontaneously. The trial implant is removed and the actual sterilized implant 10 is inserted. The mesh 15 is inserted over the implant 10. Suture closure of the incision with a single running suture is recommended.

After six weeks with no rejection, erythema, infection, necrosis or implant migration, the capsule formation is adequate for taking a definitive alginate impression for positioning of the prosthesis so as to ensure anterior registration with the implants and coupling with the magnets. An entire bilateral alginate impression is made of the chest from the suprasternal notch superiorly to the bilateral axillas and inferiorly to the umbilicus.

In the case of a breast prosthesis, the alginate impression is used to form the posterior 41 of the breast prosthesis 40. The anterior 42 of the breast prosthesis and the entire breast prosthesis may be formed by the method disclosed in U.S. Pat. No. 5,376,323, which is incorporated herein by reference, in order to replicate the appearance of the natural breast. The prosthesis is formed with a plurality of flexible carriers 20 as described below with reference to FIGS. 1–4.

The flexible carrier 20, desirably made of silastic, is formed with a hollow cylindrical portion 21 to hold a permanent magnet 30, such as a neodymium type. The cylindrical portion 21 comprises a circular end cap 22 and a cylindrical wall 23. The cylindrical wall 23 is further provided with a peripheral flange portion 24 attached to an edge of the cylindrical wall 23 opposite to the end cap 22. The hollow interior of the cylindrical portion 21 is sized to allow the permanent magnet 30 to move freely back and forth.

A recess 25 is formed around the interior of the flange portion 24 for receiving a mesh 31 which is desirably made of Teflon. The mesh 31 may also be made of other biocompatible material such as polypropylene.

Figure 3:
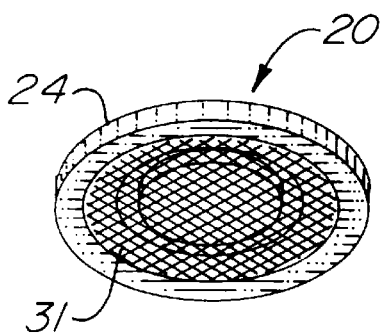
FIG. 3 is an isometric view of the assembled flexible carrier.
Figure 4:
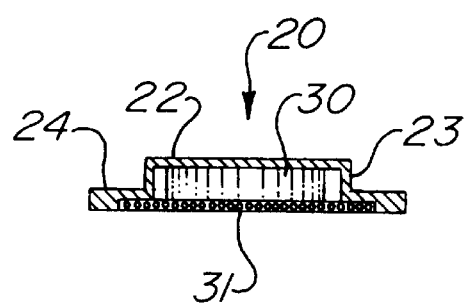
FIG. 4 is a sectional side elevational view of the assembled flexible carrier of FIG. 3.

The hollow cylindrical portion 21 is assembled with the magnet 30 and and the mesh 31 into the flexible carrier 20 as shown in FIGS. 3 and 4.

A plurality of flexible carriers 20 are formed into the anterior 41 of the prosthesis 40 as shown in FIGS. 6–8 so that the prosthesis 40, when placed next to the skin 14 of the user, aligns with the previously implanted surgical steel implants 10 as shown in FIG. 5. Forming the flexible carriers 20 into the prosthesis 40 may be accomplished simply by placing the flexible carriers into the mold in which the prosthesis is formed prior to injecting the mold with the material from which the prosthesis is formed. This process is facilitated if the flexible carriers 20 and the prosthesis 40 are formed of the same or similar materials, such as room temperature vulcanizable silicon, including silastic.

Since the magnets 30 are allowed a certain degree of freedom of movement within the flexible carriers 20, the prosthesis 40 is allowed to flex and move with respect to the user's skin 14 without unnecessary binding. Furthermore, the flexible carrier 20 itself is desirably composed of flexible material thereby allowing greater overall flexibility as the carriers 20 themselves flex in addition to the compliant motion of the magnets 30 within the flexible carriers 20.

The mesh 31 over the opening of the flexible carrier 20 prevents the magnet 30 from coming into direct contact with the user's skin 14. This allows for breathability and also avoids skin strangulation from excess pressure of the magnet 30 on the surgical steel implant 10.

It may be seen that affixing the prosthesis 40 to the user is a simple matter of registering the magnets 30 with the implants 10 so that the attractive magnetic force of the magnets 30 toward the ferromagnetic implants 10 holds the prosthesis firmly but flexibly in the correct position. Removing the prosthesis is simply a matter of pulling the prosthesis away from the implants until the magnetic attraction is broken.

The present invention has been described with reference to certain preferred and alternative embodiments that are intended to be exemplary only and not limiting to the full scope of the present invention as set forth in the appended claims.

What is claimed is:

1. An external breast prosthesis for removable attachment to the body of a user having received ferromagnetic implants at a site of attachment, comprising:

an anatomical portion replicating at least some of the characteristics of a breast; and a body facing portion attached to the anatomical portion and shaped to conform substantially to the surface anatomy of the body at a site of attachment, said body facing portion comprising at least one carrier;

each of said at least one carrier comprising compliant housing means affixed to said body facing portion and a permanent magnet for magnetic attachment to a respective one of said ferromagnetic implants whereby said permanent magnet is housed within said compliant housing means so as to allow movement of said permanent magnet within said compliant housing means, said compliant housing means further having a body facing opening and a mesh covering said body facing opening.

2. The external prosthesis of claim 1, wherein said compliant housing means comprises a circular end cap comprising an essentially flat circular plate having a perimeter, a cylindrical wall having first and second circular edges, said first circular edge being attached to said perimeter of said circular end cap, and a peripheral flange attached to said second circular edge of said cylindrical wall.

3. The external prosthesis of claim 1, wherein said compliant housing means is formed of flexible material.

4. The external prosthesis of claim 3 wherein said flexible material comprises room temperature vulcanizable silicone.

5. A method of removably attaching an external breast prosthesis to the body of a user, comprising the steps of:

surgically implanting at least one ferromagnetic implant beneath the skin of the user at a site of attachment;

taking an impression of the site of attachment;

preparing a mold for forming an external prosthesis comprising an anatomical portion replicating at least some of the characteristics of a breast and a body facing portion shaped from said impression to conform substantially to the surface anatomy of the body at the site of attachment placing in said mold at least one carrier adjacent to said body facing portion so as to align each of said at least one carrier with a respective site of implantation of one of said at least one ferromagnetic implant; each of said at least one carrier comprising a permanent magnet and compliant housing means affixed to said body facing portion whereby said permanent magnet is housed within said compliant housing means so as to allow movement of said permanent magnet within said compliant housing means, said compliant housing means further having a body facing opening and a mesh covering said body facing opening;

injecting said mold with room temperature vulcanizable silicone;

allowing said room temperature vulcanizable silicone to cure;

removing said external prosthesis from said mold; and removably attaching said external prosthesis to the body of the user by aligning each of said at least one carrier with a respective one of said at least one ferromagnetic implant.

6. The method of claim 5 wherein the step of surgically implanting at least one ferromagnetic implant beneath the skin of the user at a site of attachment further comprises the step of placing a biocompatible mesh above each of said at least one ferromagnetic implant.

7. A kit for removable attachment of an external prosthesis to the body of a user, comprising:

an external prosthesis for removable attachment to the body of a user, said external prosthesis comprising an anatomical portion replicating at least some of the characteristics of a breast; and a body facing portion attached to the anatomical portion and shaped to conform substantially to the surface anatomy of the body at a site of attachment, said body facing portion comprising at least one carrier;

each of said at least one carrier comprising a permanent magnet and compliant housing means affixed to said body facing portion whereby said permanent magnet is housed within said compliant housing means so as to allow movement of said permanent magnet within said compliant housing means, said compliant housing means further having a body facing opening and a mesh covering said body facing opening; and at least one ferromagnetic implant for implantation at said site of attachment on the body of the user whereby each of said permanent magnets is aligned with a respective one of said at least one ferromagnetic implant.

8. The kit of claim 7, wherein said compliant housing means comprises a circular end cap comprising an essentially flat circular plate having a perimeter, a cylindrical wall having first and second circular edges, said first circular edge being attached to said perimeter of said circular end cap, and a peripheral flange attached to said second circular edge of said cylindrical wall.

9. The kit of claim 7, wherein said compliant housing means is formed of flexible material.

10. The kit of claim 9 wherein said flexible material comprises room temperature vulcanizable silicone.

11. The kit of claim 7, wherein said ferromagnetic implant comprises a core of ferromagnetic material, a corrosion product containment layer covering said core, and a biocompatible layer covering said corrosion product containment layer.

12. The kit of claim 11 wherein said core of ferromagnetic material comprises stainless steel.

13. The kit of claim 12 wherein said corrosion product containment layer comprises methylmethacrylate.

14. The kit of claim 13 wherein said biocompatible layer comprises silicone.

15. The kit of claim 7 further comprising a biocompatible mesh for implantation above each of said ferromagnetic implants.

16. An external prosthesis for removable attachment to the body of a user having received ferromagnetic implants at a site of attachment, comprising:

an anatomical portion replicating at least some of the characteristics of an anatomical feature of the head and neck region of the body of the user; and a body facing portion attached to the anatomical portion and shaped to conform substantially to the surface anatomy of the body at a site of attachment, said body facing portion comprising at least one carrier;

each of said at least one carrier comprising a compliant housing means affixed to said body facing portion and a permanent magnet for magnetic attachment to a respective one of said ferromagnetic implants whereby said permanent magnet is housed within said compliant housing means so as to allow movement of said permanent magnet within said compliant housing means, said compliant housing means further having a body facing opening and a mesh covering said body facing opening.

17. The external prosthesis of claim 16, wherein said compliant housing means comprises a circular end cap comprising an essentially flat circular plate having a perimeter, a cylindrical wall having first and second circular edges, said first circular edge being attached to said perimeter of said circular end cap, and a peripheral flange attached to said second circular edge of said cylindrical wall.

18. The external prosthesis of claim 16, wherein said compliant housing means is formed of flexible material.

19. The external prosthesis of claim 18 wherein said flexible material comprises room temperature vulcanizable silicone.

20. A method of removably attaching an external prosthesis to the body of a user, comprising the steps of:

surgically implanting at least one ferromagnetic implant beneath the skin of the user at a site of attachment;

taking an impression of the site of attachment;

preparing a mold for forming an external prosthesis comprising an anatomical portion replicating at least some of the characteristics of an anatomical feature of the head and neck region of the body of the user and a body facing portion shaped from said impression to conform substantially to the surface anatomy of the body at the site of attachment;

placing in said mold at least one carrier adjacent to said body facing portion so as to align each of said at least one carrier with a respective site of implantation of one of said at least one ferromagnetic implant; each of said at least one carrier comprising a permanent magnet and compliant housing means affixed to said body facing portion whereby said permanent magnet is housed within said compliant housing means so as to allow movement of said permanent magnet within said compliant housing means, said compliant housing means further having a body facing opening and a mesh covering said body facing opening;

injecting said mold with room temperature vulcanizable silicone;

allowing said room temperature vulcanizable silicone to cure;

removing said external prosthesis from said mold; and removably attaching said external prosthesis to the body of the user by aligning each of said at least one carrier with a respective one of said at least one ferromagnetic implant.

21. The method of claim 20 wherein the step of surgically implanting at least one ferromagnetic implant beneath the skin of the user at a site of attachment further comprises the step of placing a biocompatible mesh above each of said at least one implant.

22. A kit for removable attachment of an external prosthesis to the body of a user, comprising:

an external prosthesis for removable attachment to the body of a user, said external prosthesis comprising an anatomical portion replicating at least some of the characteristics of an anatomical feature of the head and neck region of the body of the user; and a body facing portion attached to the anatomical portion and shaped to conform substantially to the surface anatomy of the body at a site of attachment, said body facing portion comprising at least one carrier;

each of said at least one carrier comprising a permanent magnet and compliant housing means affixed to said body facing portion whereby said permanent magnet is housed within said compliant housing means so as to allow movement of said permanent magnet within said compliant housing means, said compliant housing means further having a body facing opening and a mesh covering said body facing opening; and at least one ferromagnetic implant for implantation at said site of attachment on the body of the user whereby each of said permanent magnets is aligned with a respective one of said one of said at least one ferromagnetic implant.

23. The kit of claim 22, wherein said compliant housing means comprises a circular end cap comprising an essentially flat circular plate having a perimeter, a cylindrical wall having first and second circular edges, said first circular edge being attached to said perimeter of said circular end cap, and a peripheral flange attached to said second circular edge of said cylindrical wall.

24. The kit of claim 22, wherein said compliant housing means is formed of flexible material.

25. The kit of claim 24 wherein said flexible material comprises room temperature vulcanizable silicone.

26. The kit of claim 22, wherein said ferromagnetic implant comprises a core of ferromagnetic material, a corrosion product containment layer covering said core, and a biocompatible layer covering said corrosion product containment layer.

27. The kit of claim 26 wherein said core of ferromagnetic material comprises stainless steel.

28. The kit of claim 27 wherein said corrosion product containment layer comprises methylmethacrylate.

29. The kit of claim 28 wherein said biocompatible layer comprises silicone.

30. The kit of claim 22 further comprising a biocompatible mesh for implantation above each of said ferromagnetic implants.

* * * * *